United States Patent [19]

Dean et al.

[11] Patent Number: 5,127,272
[45] Date of Patent: Jul. 7, 1992

[54] MULTIPHASE FLOW RATE MONITORING MEANS AND METHOD

[75] Inventors: Timothy L. Dean, London, United Kingdom; Earl L. Dowty, Katy, Tex.; Startup Ian, Tunbridge Wells, United Kingdom

[73] Assignees: Texaco Ltd.; Texaco Inc., both of White Plains, N.Y.

[21] Appl. No.: 637,024

[22] Filed: Jan. 3, 1991

[51] Int. Cl.$^5$ .......................... G01F 1/74; G01F 15/08
[52] U.S. Cl. ...................... 73/861.04; 73/200
[58] Field of Search .............................. 73/200, 861.04

[56] References Cited

U.S. PATENT DOCUMENTS 4,760,742  8/1988  Hatton ............................... 73/861.04
4,881,412  11/1989  Northedge ........................ 73/861.04

*Primary Examiner*—Herbert Goldstein
*Attorney, Agent, or Firm*—Robert A. Kulason; James J. O'Loughlin; Ronald G. Gillespie

[57] ABSTRACT

The flow rate monitor includes a test line containing a chamber wherein the test line is declinated at a predetermined angle so stratification of liquid and gas will occur in the chamber. A sample stream is removed from the liquid in the chamber and provided to a separator which separates the gas from the sample stream to provide a gas output and a liquid output. The gas output and the liquid output is returned to the test line. The water cut of the liquid output is determined while the pressure of the composite petroleum stream is sensed along with the temperature. The volumetric flow rate of the composite petroleum stream is monitored and the flow rate signal is provided. The density of the composite petroleum stream is also monitored. The flow rate of all three coponents of the composite petroleum stream is determined in accordance with the temperature signal, the pressure signal, the water cut signal, the flow rate signal and the density signal.

8 Claims, 1 Drawing Sheet

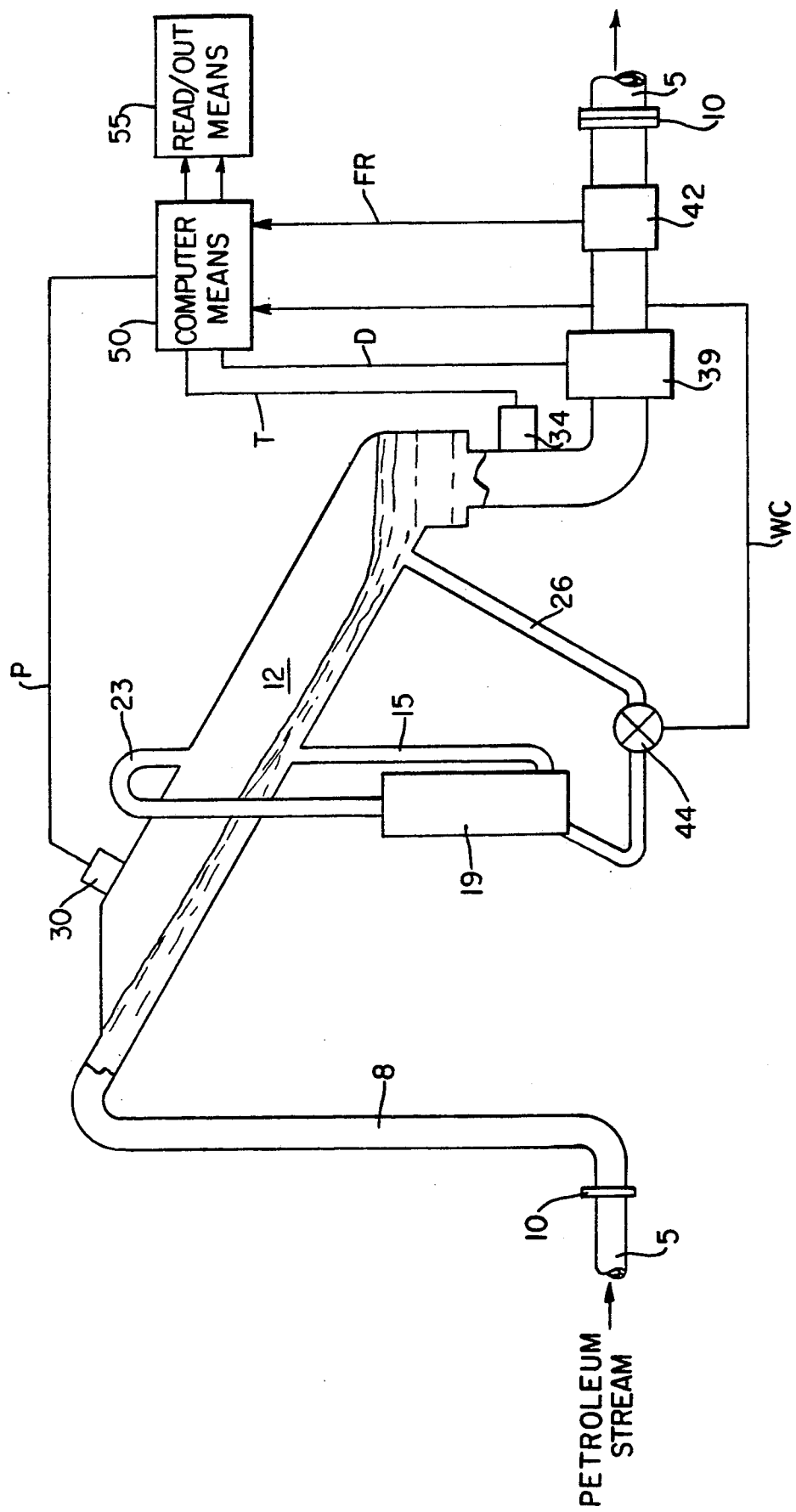

MULTIPHASE FLOW RATE MONITORING MEANS AND METHOD

BACKGROUND OF THE INVENTION

FIELD OF THE INVENTION

The present invention relates to petroleum stream analyzers.

SUMMARY OF THE INVENTION

The flow rate monitor, of the present invention, monitors a composite petroleum stream and includes a test line containing a chamber wherein the test line and chamber are declinated at a predetermined angle so that stratification of the composite petroleum stream into liquid and gas fractions will occur in the chamber. A sample stream is removed from the liquid in the chamber and provided to a separator which separates the entrained gas from the sample stream to provide a gas output and a liquid output. The gas output and the liquid output are returned to the test line. The water cut of the liquid output is determined while the pressure of the composite petroleum stream is sensed along with the temperature. The volumetric flow rate of the composite petroleum stream is monitored and a flow rate signal is provided. The density of the composite petroleum stream is also monitored. The volumetric flow rates of all three components of the composite petroleum stream are determined in accordance with the temperature signal, the pressure signal, the water cut signal, the flow rate signal and the density signal.

The objects and advantages of the invention will appear more fully hereinafter, from a consideration of the detailed description which follows, taken together with the accompanying drawing, wherein one embodiment is illustrated by way of example. It should be expressly understood, however, that the drawing is for illustration purposes only and is not to be construed as defining the limits of the invention.

DESCRIPTION OF THE DRAWING

The drawing is in part a simplified block diagram and in part schematic showing a flow rate monitor, constructed in accordance with the present invention, for a multiphase petroleum stream.

DESCRIPTION OF THE INVENTION

The present invention represents a new design for metering gas, oil and water/brine production rates that will perform at least equal to, or better than conventional designs. It should be noted that the word "water" shall be used hereinafter in lieu of "water/brine" and shall cover any water regardless of salinity. Furthermore, the design of the present invention is more reliable and can be made more compact and less expensive than commercially available metering systems. The present invention is suitable for measuring the individual flow rates of oil, gas and water components of a multiphase petroleum stream, such as a composite production stream from an oil well. The meter is suitable for installation subsea, at the surface of the sea, on an offshore platform, or onshore. The meter can be sized to accommodate wide ranges of liquid and gas flow rates with water cuts from zero to 100 percent.

Referring now to the Figure, there is shown a pipeline 5 connected to a test line 8, as indicated by flanges 10. Test line 8 rises vertically and then slopes down at a predetermined angle sufficient to stratify the composite petroleum stream. At the end of the sloping portion of test line 8, the diameter is increased substantially so as to form a chamber 12 before going to a vertical descent. Test line 8 is turned through 90° from the vertical portion to a horizontal direction before reconnection to pipeline 5. The composite petroleum stream, while passing through test line 8, will tend to stratify by the action of gravity such that liquid flows along the bottom of the sloping pipe with gas flowing along the top. A sample stream of the liquid component of the composite petroleum stream containing some entrained gas is removed by a sampling line 15 and provided to a separator 19. Separator 19 allows the entrained gas in the sample stream to separate from the liquid and be returned to the gas portion of test line 8 via line 12.

The liquid portion of the sample stream in line 15 is returned to the production stream in chamber 12 through a line 26. During the flowing of the petroleum stream through pipeline 5 and test line 8, certain parameters are measured. One parameter is pressure, which is being sensed by a pressure sensor 30 providing a signal P corresponding to the sensed pressure. A temperature sensor 34 senses the temperature of the liquid flowing in test line 8 just prior to entering pipeline 5 again. Temperature sensor 34 provides a signal T corresponding to the sensed temperature. Also in the discharge portion of test line 8, a densitometer 39 provides a signal D corresponding to the density of the fluid exiting pipeline 5.

A volumetric flowmeter 42 senses the flow rate of the petroleum stream re-entering pipeline 5 and provides a corresponding signal FR. A net oil or water cut meter 44 provides a signal WC corresponding to the net oil or water cut of the sample stream exiting separator 19.

Signals P, T, D, FR and WC, are provided to computer means 50, which provides signals to readout means 55 corresponding to the flow rates of the oil, water and gas.

Computer means solves the following equations:

$$X \text{ gas} = \{D \text{ comp} - \{D \text{ oil} (1-X_{H2O}) + D_{H2O}(H_{H2O})\}/\{D \text{ gas} - \{D \text{ oil}(1-X_{H2O}) + D_{H2O}(X_{H2O})\}\} \quad (1)$$

where X gas is the volumetric gas fraction of the composite petroleum stream at its actual pressure and temperature, $X_{H2O}$ is the volumetric water fraction (water cut) of the oil and water components of the composite petroleum stream at their actual temperature and pressure (measured by monitors 44), D comp is the density of the composite petroleum stream at its actual pressure and temperature (measured by densitometer 39), D gas is the density of the gas component of the composite petroleum stream at its actual temperature and pressure (determined from PVT data for the gas and oil of the composite petroleum stream at its actual pressure and temperature), D oil is the density of the oil component of the composite petroleum stream at its actual pressure and temperature (determined from PVT data for the gas and oil of the composite petroleum stream), and $D_{H2O}$ is the density of the water component of the composite petroleum stream at its actual pressure and temperature. Obviously, from the foregoing, the various PTV density values are stored in computer means 50 memory and computer means 50 uses the stored values as required.

$$Q \text{ gas} = (X \text{ gas}) (Q \text{ comp}), \quad (2)$$

$$Q_{H2O} = X_{H2O}(Q \text{ comp} - Q \text{ gas}), \quad (3)$$

$$Q \text{ oil} = (1 - X_{H2O})(Q \text{ comp} - Q \text{ gas}), \quad (4)$$

where Q comp is the volumetric flow rate at its actual pressure and temperature (measured by volumetric flowmeter 42), Q gas is the volumetric flow rate of the gas component of the composite petroleum stream at its actual pressure and temperature, Q oil is the volumetric flow rate of the oil component of the composite petroleum and $Q_{H2O}$ is the volumetric flow rate of the water component at its actual temperature and pressure.

What is claimed is:

1. A flow rate means for monitoring a composite petroleum stream having a gas component, an oil component and a water component comprising:

a test line containing a chamber, said test line being declinated at a predetermined angle so that stratifications of liquid and gas will occur in the chamber, sampling means for providing a sample stream from the liquid in the chamber, means for separating gas from the sample stream to provide a gas output and a liquid output, means for returning the gas output and the liquid output to the test line, water cut means for determining the water cut of the liquid output and providing a water cut signal corresponding thereto, pressure means for sensing the pressure of the composite petroleum stream and providing a pressure signal corresponding thereto, temperature means for sensing the temperature of the composite petroleum stream and providing a temperature signal representative thereof, flow rate means for monitoring the volumetric flow rate of the composite petroleum stream and providing a flow rate signal corresponding thereto, density means for monitoring the density of the composite petroleum stream and providing a density signal representative thereof, and deriving means for deriving the volumetric flow rates of the components of the composite petroleum stream in accordance with the temperature signal, the pressure signal, the water cut signal, the flow rate signal and the density signal.

2. Means as described in claim 1 in which the deriving means includes;

means for storing PVT density values, and gas fraction means for deriving the volumetric gas fraction in accordance with the water cut signal, the PVT density for the composite stream, the PVT density for the oil component, and the density of the water/brine component.

3. Means as described in claim 2 in which the gas fraction means derives the volumetric gas fraction X gas in accordance with the following equation:

$$X \text{ gas} = \{D \text{ comp} - \{D \text{ oil} (1 - X_{H2O}) + D_{H2O}(H_{H2O})\}\} / \{D \text{ gas} - \{D \text{ oil} (1 - X_{H2O}) + D_{H2O}(X_{H2O})\}\} \quad (1)$$

where X gas is the volumetric gas fraction of the composite petroleum stream at its actual pressure and temperature, $X_{H2O}$ is the volumetric water/brine fraction of the oil and water components of the composite petroleum stream at their actual temperature and pressure, D comp is the density of the composite petroleum stream at its actual pressure and temperature, D gas is the density of the gas component of the composite petroleum stream at its actual temperature and pressure, D oil is the density of the oil component of the composite petroleum steam at its actual pressure and temperature, and $D_{H2O}$ is the density of water component of the composite petroleum stream at its actual pressure and temperature.

4. Means as described in claim 3 for deriving the volumetric flow rate Q gas of the gas fraction, the volumetric flow rate $Q_{H2O}$ of the water/brine fraction, and the volumetric flow rate Q oil of the oil fraction in accordance with the following formulas:

$$Q_{H2O} = X_{H2O}(Q \text{ comp} - Q \text{ gas}),$$

$$Q_{H2O} = (Q \text{ comp} - Q \text{ gas}), \text{ and}$$

$$Q \text{ oil} = (1 - X_{H2O})(Q \text{ comp} - Q \text{ gas})$$

5. A method for monitoring the component flow rates of a composite petroleum stream having a gas component, an oil component and a water component comprising the steps of:

declinating at a test line, containing a chamber, at a predetermined angle so that stratifications of liquid and gas will occur in the chamber, providing a sample stream from the liquid in the chamber, separating gas from the sample stream to provide a gas output and a liquid output, returning the gas output and the liquid output to the test line, determining the water cut of the liquid output, providing a water cut signal corresponding to the determined water cut, sensing the pressure of the composite petroleum stream, providing a pressure signal corresponding to the sensed pressure, sensing the temperature of the composite petroleum stream, providing a temperature signal representative of the sensed temperature, monitoring the volumetric flow rate of the composite petroleum stream, providing a flow rate signal corresponding to the monitored flow rate, monitoring the density of the composite petroleum stream providing a density signal representative of the monitored density, and deriving the volumetric flow rates of the components of the composite petroleum stream in accordance with the temperature signal, the pressure signal, the water cut signal, the flow rate signal and the density signal.

6. A method as described in claim 5 in which the deriving step includes:

storing PVT density values, and deriving the volumetric gas fraction in accordance with the water cut signal, the PVT density for the composite stream, the PVT density for the oil component, and the density of the water/brine component.

7. A method as described in claim 6 in which the gas fraction step derives the volumetric gas fraction X gas in accordance with the following equation:

$$X_{gas} = \{D_{comp} - \{D_{oil}(1 - X_{H2O}) + D_{H2O}(H_{H2O})\}\}/\{D_{gas} - \{D_{oil}(1 - X_{H2O}) + D_{H2O}(X_{H2O})\}\} \quad (1)$$

Where $X_{gas}$ is the volumetric gas fraction of the composite petroleum stream at its actual pressure and temperature, $X_{H2O}$ is the volumetric water cut of the sample stream at its actual temperature and pressure $D_{comp}$ is the density of the composite petroleum stream at its actual pressure and temperature, $D_{gas}$ is the density of the gas component of the composite petroleum stream at its actual temperature and pressure (determined from PVT data for the gas and oil of the composite petroleum stream at its actual pressure and temperature), $D_{oil}$ is the density of the oil component of the composite petroleum stream at its actual pressure and temperature (determined from PVT data for the gas and oil of the composite petroleum stream), and $D_{H2O}$ is the density of water component of the composite petroleum stream at its actual pressure and temperature.

8. A method as described in claim 7 in which the step volumetric flow rates includes deriving the volumetric flow rate $Q_{gas}$ of the gas fraction, the volumetric flow rate $Q_{H2O}$ of water fraction, and the volumetric flow rate $Q_{Oil}$ of the oil fraction in accordance with the following formulas:

$$Q_{gas} = (X_{gas})(Q_{comp}),$$

$$Q_{H2O} = X_{H2O}(Q_{comp} - Q_{gas})$$

$$Q_{oil} = (1 - X_{H2O})(Q_{comp} - Q_{gas})$$

* * * * *